United States Patent
Nakazawa et al.

(10) Patent No.: US 7,294,707 B2
(45) Date of Patent: Nov. 13, 2007

(54) METHOD FOR MODIFYING PROTEIN OR PEPTIDE C-TERMINAL

(75) Inventors: Takashi Nakazawa, Nara (JP); Minoru Yamaguchi, Kyoto (JP); Hiroki Kuyama, Kyoto (JP); Eiji Ando, Kyoto (JP); Norikazu Ueyama, Osaka (JP); Taka-aki Okamura, Osaka (JP); Shigemi Norioka, Ibaraki (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 10/958,298

(22) Filed: Oct. 6, 2004

(65) Prior Publication Data

US 2005/0085622 A1    Apr. 21, 2005

(30) Foreign Application Priority Data

Oct. 17, 2003  (JP) ............................. 2003-357787
Mar. 31, 2004  (JP) ............................. 2004-105644

(51) Int. Cl.
*C07K 1/00* (2006.01)

(52) U.S. Cl. .................................... 530/402

(58) Field of Classification Search ............... 530/350; 514/12; 435/7.1, 69.1
See application file for complete search history.

(56) References Cited

U.S. PATENT DOCUMENTS 5,468,843 A * 11/1995 Boyd et al. ................. 530/345

FOREIGN PATENT DOCUMENTS

EP    0463520    *  1/1992
JP    10-293130 A1    11/1998

OTHER PUBLICATIONS

Goodman and Levine, "Peptide Synthesis via Active Esters. IV. Racemization □□and Ring-Opening Reactions of Optically Active Oxazolones", 1964, J. Am. Chem. Soc., vol. 86, pp. 2918-2922.*

* cited by examiner

*Primary Examiner*—Robert B. Mondesi
(74) *Attorney, Agent, or Firm*—Rader, Fishman & Grauer PLLC

(57) ABSTRACT

A simple and low-cost method of selectively modifying the C-terminal of a protein or peptide is provided. A method of modifying the C-terminal of a protein or peptide comprises forming an intramolecular oxazolone ring at the C-terminal of the protein or peptide that requires C-terminal modification, and then performing a ring-opening of the oxazolone ring to produce a protein or peptide with a modified C-terminal. Preferred forms include a method in which by reacting the oxazolone ring with a compound containing a nucleophilic group to effect an oxazolone ring-opening, a protein or peptide is produced in which the C-terminal is modified with the compound containing the nucleophilic group, as well as a method in which by reacting the oxazolone ring with an active esterifying agent to effect a ring-opening, the oxazolone is converted to an active ester, which by subsequent reaction with a compound containing a nucleophilic group, produces a protein or peptide in which the C-terminal has been modified with the compound containing the nucleophilic group.

11 Claims, 3 Drawing Sheets

METHOD FOR MODIFYING PROTEIN OR PEPTIDE C-TERMINAL

BACKGROUND OF THE INVENTION

1. Field of the Invention

The present invention relates to the field of protein and peptide chemistry.

2. Disclosure of the Related Art

Conventional methods for modifying the C-terminal of a protein or peptide, using a compound containing a nucleophilic group such as an amino group, hydroxyl group, or thiol group, have involved using a material such as 1-ethyl-3-(3-dimethylaminopropyl)-carbodiimide hydrochloride (EDC) or N-hydroxysuccinimide (NHS) to effect an active esterification of the C-terminal of the protein or peptide, and then conducting a reaction with an amino group. However, these reagents also react with side chain carboxyl groups contained within aspartic acid residues or glutamic acid residues in the protein or peptide, meaning that in order to ensure selective modification of the C-terminal, the side chain carboxyl groups of these amino acid residues must first be protected.

Japanese Laid-open Patent Publication No. 10-293130 (1998) discloses a method of determining the amino acid sequence from the C-terminal of a protein or peptide by converting the C-terminal of the protein or peptide to an oxazolone, liberating the C-terminal amino acid, and then repeating the operation of separating and identifying the produced amino acid.

SUMMARY OF THE INVENTION

An object of the present invention is to provide a simple and low-cost method of selectively modifying the C-terminal of a protein or peptide.

The present inventors made eager investigation. As a result, the present inventors have found out that they can achieve the above object by modifying the C-terminal of a protein or peptide using an oxazolone ring forming reaction. Thus, the present invention has been made.

The present invention comprises the following inventions:

(1) A method for modifying the C-terminal of a protein or peptide, the method comprising the steps of: forming an intramolecular oxazolone ring at the C-terminal of the protein or peptide that requires C-terminal modification, and performing a ring-opening of the oxazolone ring to produce a protein or peptide with a modified C-terminal.

The aspects (2) to (6) listed below relate to an embodiment of the present invention in which, following formation of the oxazolone ring, the protein or peptide with a modified C-terminal is formed concurrently with the ring-opening of the oxazolone ring.

(2) The method for modifying the C-terminal of a protein or peptide according to (1), wherein by reacting the oxazolone ring with a compound containing a nucleophilic group to effect a ring-opening, a protein or peptide is produced in which the C-terminal is modified with the compound containing the nucleophilic group.

(3) The method for modifying the C-terminal of a protein or peptide according to (2), wherein the nucleophilic group is selected from the group consisting of an amino group, a hydroxyl group, and a thiol group.

(4) The method for modifying the C-terminal of a protein or peptide according to anyone of (1) to (3), wherein the oxazolone ring is formed through the action of an acid anhydride.

(5) The method for modifying the C-terminal of a protein or peptide according to any one of (1) to (4), wherein the oxazolone ring is formed through the action of acetic anhydride.

(6) The method for modifying the C-terminal of a protein or peptide according to any one of (2) to (5), wherein the compound containing the nucleophilic group is reacted in the presence of a base.

The aspects (7) to (12) listed below relate to an embodiment of the present invention in which, following formation of the oxazolone ring, the oxazolone first undergoes a ring-opening to form an active ester, which is subsequently used to produce a protein or peptide with a modified C-terminal.

(7) The method for modifying the C-terminal of a protein or peptide according to (1), wherein by reacting the oxazolone ring with an active esterifying agent to effect a ring-opening, the oxazolone is converted to an active ester, which by subsequent reaction with a compound containing a nucleophilic group, produces a protein or peptide in which the C-terminal is modified with the compound containing the nucleophilic group.

(8) The method for modifying the C-terminal of a protein or peptide according to (7), wherein the nucleophilic group is selected from the group consisting of an amino group, a hydroxyl group, and a thiol group.

(9) The method for modifying the C-terminal of a protein or peptide according to any one of (1), (7) and (8), wherein the oxazolone ring is formed through the action of a mixture of an acid anhydride and a carboxylic acid.

(10) The method for modifying the C-terminal of a protein or peptide according to (9), wherein the acid anhydride is acetic anhydride.

(11) The method for modifying the C-terminal of a protein or peptide according to either one of (9) and (10), wherein the carboxylic acid is formic acid.

(12) The method for modifying the C-terminal of a protein or peptide according to any one of (7) to (11), wherein the active esterifying agent is selected from the group consisting of pentafluorophenol, 4-sulfo-2,3,5,6-tetrafluorophenol, p-nitrophenol, N-hydroxysuccinimide, and N-hydroxybenzotriazole.

According to the present invention, a simple and low-cost method of selectively modifying the C-terminal of a protein or peptide can be provided. The present invention offers a significant advantage in that by using an oxazolone ring forming reaction, selective modification of the C-terminal can be conducted without having to conduct a pretreatment to protect the protein or peptide side chains within a biological sample.

DETAILED DESCRIPTION OF THE INVENTION

Figure 1:
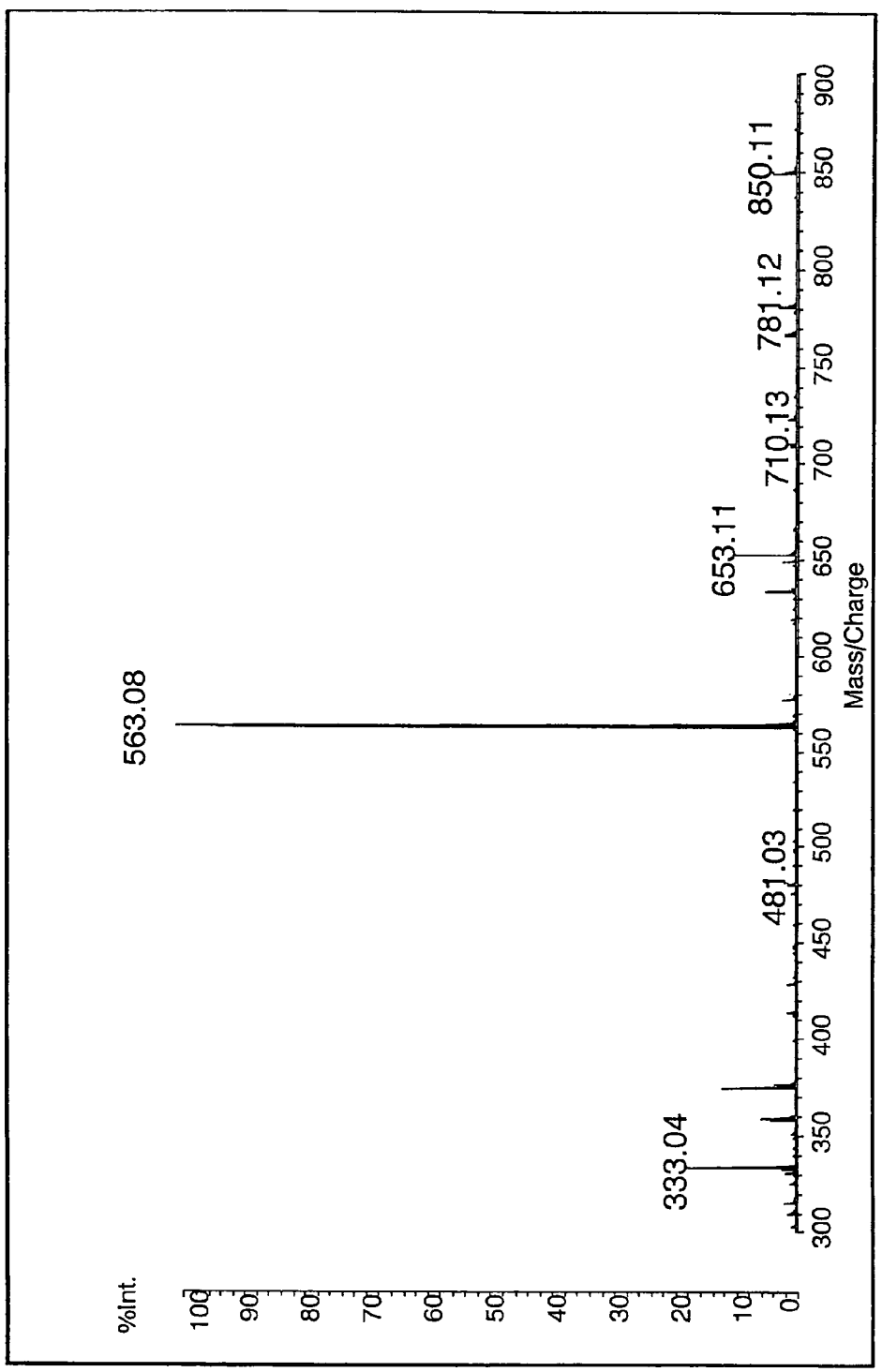
FIG. 1 is a MALDI-TOF MS spectrum obtained in an example of the present invention.

The present invention provides a method for modifying the C-terminal of a protein or peptide using an oxazolone ring forming reaction. In other words, in the present invention, an oxazolone ring is formed at the C-terminal end of the protein or peptide, and by using an appropriate method to subsequently open this ring, a protein or peptide with a modified C-terminal can be produced. During the oxazolone ring-opening, the protein or peptide with a modified C-terminal can either be formed concurrently with the ring-opening reaction (a first embodiment), or alternatively, the ring-opening can be used to first generate an active ester, which is subsequently used to produce the protein or peptide with a modified C-terminal (a second embodiment). As follows is a detailed description of the present invention, using these first and second embodiments as examples of the present invention.

First is a description of the first embodiment, in which following formation of the oxazolone ring, the protein or peptide with a modified C-terminal is formed concurrently with the ring-opening of the oxazolone ring.

In the present invention, the first step involves conducting a reaction to form an intramolecular oxazolone ring at the C-terminal residue of the protein or peptide that requires C-terminal modification. An example of this reaction is shown below in equation (I). In equation (I), the action of acetic anhydride is used to form the oxazolone ring.

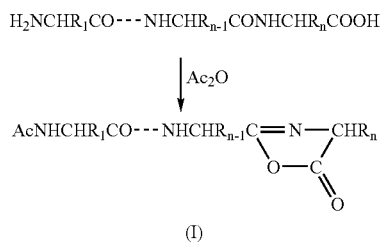

(I)

In this reaction, an oxazolone ring is not formed at the side chain carboxyl groups contained within aspartic acid residues or glutamic acid residues. Accordingly, by employing this oxazolone ring forming reaction, the present invention enables the C-terminal of the protein or peptide to be modified selectively. In other words, unlike conventional methods, there is no need to protect the side chain carboxyl groups of the protein or peptide.

The reaction for forming the oxazolone ring is conducted by reacting the protein or peptide with an oxazolone ring forming reagent.

This oxazolone ring forming reagent is preferably an acid anhydride. Examples of suitable acid anhydrides include acetic anhydride, trifluoroacetic anhydride, benzoic anhydride, ortho-sulfobenzoic anhydride, and propionic anhydride. These anhydrides may be used alone or in combination of two or more thereof. In the present invention, the use of acetic anhydride is particularly preferred. The use of an acid anhydride reagent is preferred for the following reasons. Firstly, these reagents are cheap and stable, and secondly, the removal of excess reagent following completion of the reaction is simple. Namely, removal of the excess reagent does not require the use of column chromatographic techniques such as gel filtration as in conventional methods, but can be simply achieved by vacuum drying.

The quantity of reagent used for forming the oxazolone ring is typically at least 1 equivalent relative to the peptide. The reagent can be used without solvent. The reaction is typically conducted under conditions including a temperature within a range from room temperature to 200° C., and a reaction time from 1 minute through to an overnight reaction. These conditions can be determined properly by the skilled person. Removal of any excess acetic anhydride following completion of the reaction can be carried out under reduced pressure.

Subsequently, the protein or peptide is reacted with a compound containing a nucleophilic group. The nucleophilic group should be a group capable of effecting a ring-opening of the oxazolone ring, such as an amino group, hydroxyl group or thiol group. An example of this reaction, which uses a compound containing an amino group as the nucleophilic group, is shown below in equation (II). This reaction causes a ring-opening of the aforementioned oxazolone ring, and an introduction of a modifying group at the C-terminal of the protein or peptide. In other words, if the compound containing an amino group as the nucleophilic group is represented by a general formula $XNH_2$, then the carboxyl group of the C-terminal of the protein or peptide is converted to a CONHX group. Suitable examples of this compound containing an amino group as the nucleophilic group include derivatives of the various amino acids. Examples of compounds containing a hydroxyl group as the nucleophilic group include derivatives of amino acids with a side chain hydroxyl group such as serine, threonine, and tyrosine. Examples of compounds containing a thiol group as the nucleophilic group include derivatives of amino acids with a side chain thiol group such as cysteine. These amino acid derivatives may also be peptides or proteins.

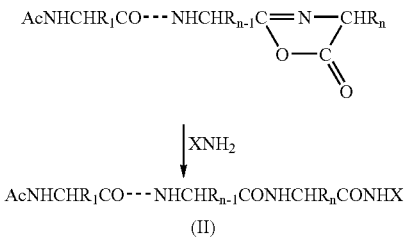

(II)

This reaction can be performed by stirring the protein or peptide that has already undergone the oxazolone ring forming reaction described above, and the compound containing the nucleophilic group, in the presence of a base.

The compound containing the nucleophilic group is typically used in a quantity within a range from 1 to 100 equivalents relative to the peptide, and can be used either in solution form, or as a suspension. Examples of suitable solvents or liquids for suspension for forming the solution or suspension include dimethylformamide, dimethylsulfoxide, dimethylacetamide, and N-methylpyrrolidone. These may be used alone or in combination of two or more thereof. If these types of organic solvent are used, then sufficient solvent is added to form a solution or suspension in which the concentration of the compound containing the nucleophilic group is within a range from 0.01 to 50% by weight.

Suitable examples of the base include triethylamine, N-methylmorpholine, trimethylamine, and diisopropylethylamine. These may be used alone or in combination of two or more thereof. The quantity of base used is within a range from 1 to 100 equivalents relative to the protein or peptide. The compound containing the nucleophilic group may also be dissolved or suspended in this base instead of being dissolved or suspended in an organic solvent as described above. Furthermore, the compound may also be dissolved or suspended in a mixture of an organic solvent and the base. The reaction is typically conducted under conditions including a temperature within a range from 0 to 200° C., and a reaction time from 1 minute through to an overnight reaction. These conditions can be determined properly by the skilled person. Removal of excess base following completion of the reaction can be carried out under reduced pressure.

Next is a description of a second embodiment, in which the oxazolone ring first undergoes a ring-opening to form an active ester, which is subsequently used to produce a protein or peptide with a modified C-terminal.

The method of the first embodiment is extremely efficient in the case of non-aqueous systems. However, in some cases, side reactions such as dehydration reactions of peptide side chain functional groups, sequential decomposition of the peptide chain, or Dakin-West reactions can occur, and as a result, the oxazolone ring formation is preferably conducted under the conditions described below. Namely, in the present invention, a mixture of an acid anhydride and a carboxylic acid (that is, an acid-acid anhydride mixture) is preferably used as the reagent for forming the oxazolone ring. Suitable examples of the carboxylic acid include formic acid, acetic acid, and trifluoroacetic acid, although as described below, if the ease with which the action of the carboxylic acid can cause an acyl group elimination within a peptide side chain functional group is considered, then formic acid is preferred.

The acid anhydride can use the same compounds as those described in the first embodiment. One example of a particularly preferred acid-acid anhydride mixture is a mixture formed from formic acid and acetic anhydride.

The mixing ratio in the carboxylic acid-acid anhydride mixture, reported as a volumetric ratio, is typically within a range from 1:10 to 10:1, and preferably from 1:2 to 2:1. In the present invention, a mixing ratio of 1:1 is particularly preferred.

When this type of acid-acid anhydride mixture is used for performing oxazolone ring formation, the reaction is typically conducted under conditions including a temperature within a range from 0 to 200° C., and a reaction time from 1 minute through to an overnight reaction. These conditions can be determined properly by the skilled person. Removal of excess acid-acid anhydride mixture following completion of the reaction can be performed easily under reduced pressure.

Using a mixture of a carboxylic acid and an acid anhydride offers the additional advantages described below.

Firstly, the types of carboxylic acids described above are able to readily dissolve most proteins and peptides, thus significantly expanding the range of materials to which the present invention can be applied.

Secondly, by using an acid-acid anhydride mixture, the oxazolone can be generated at a lower temperature than that required in the method of the first embodiment, which uses only an acid anhydride, thus suppressing a large number of the side reactions mentioned above.

The oxazolone ring forming reaction using a mixture of a carboxylic acid and an acid anhydride is preferably conducted in the presence of an active esterifying agent. In other words, by adding an active esterifying agent to the single reaction solution, the generated oxazolone ring can be more rapidly converted to an active ester. This active esterification reaction can be conducted under the same conditions as those described above for the oxazolone ring forming reaction.

The active esterifying agent can use the types of compounds typically used in peptide syntheses, comprising a hydroxyl group with comparatively high acidity. Specific examples include pentafluorophenol, 4-sulfo-2,3,5,6-tetrafluorophenol, p-nitrophenol, N-hydroxysuccinimide (HNOSu), and N-hydroxybenzotriazole (HOBt). These compounds can be properly selected by the skilled person in accordance with factors such as the solvent used and the reaction conditions. For example, pentafluorophenol and 4-sulfo-2,3,5,6-tetrafluorophenol are preferred in one regard, as the active esters are comparatively more stable, even in aqueous solutions. In other words, these compounds offer the advantage of being able to be widely used in water-based systems, which are the most suitable systems for experiments relating to peptides.

An example of oxazolone ring formation and subsequent generation of an active ester, which uses a reaction system comprising an acid-acid anhydride mixture formed from formic acid and acetic anhydride to which pentafluorophenol has been added, is shown below in equation (III).

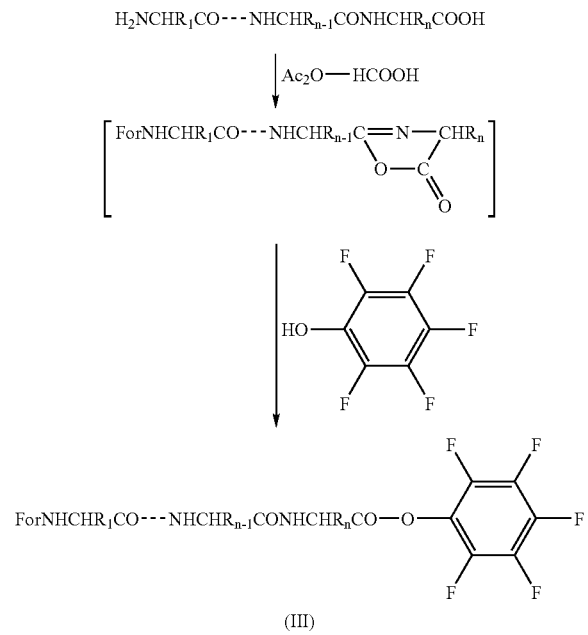

(III)

This series of reactions leading to oxazolone ring formation and subsequent generation of an active ester can be described in the following manner. In a reaction system comprising a protein or peptide that requires C-terminal modification, an acid-acid anhydride mixture, and an active esterifying agent, the oxazolone ring forming reaction between the C-terminal carboxyl group of the protein or peptide and the acid-acid anhydride mixture competes with an acylation reaction between the hydroxyl group of the active esterifying agent and the acid-acid anhydride mixture. Of these two reactions, the oxazolone ring forming reaction occurs preferentially. In other words, the C-terminal carboxyl group of the peptide undergoes preferential reaction with the acid-acid anhydride mixture, ahead of the hydroxyl group of the active esterifying agent. As a result, an oxazolone ring is formed. Subsequently, a portion of the hydroxyl groups of the active esterifying agent, which has been prevented from undergoing acylation by the preferential reaction between the C-terminal carboxyl group and the acid-acid anhydride mixture, react with the generated oxazolone, forming an active ester.

Accordingly, in an actual reaction, the ratio between the acid-acid anhydride mixture, the active esterifying agent, and the protein or peptide that requires C-terminal modification can be set in accordance with the reaction mechanism described above. The acid-acid anhydride mixture is preferably used in large excess, whereas the molar ratio between the active esterifying agent and the protein or peptide is typically set within a range from 1:10 to 1000:1, and preferably from 5:1 to 50:1. In the present invention, a molar ratio of approximately 20:1 is particularly preferred. The large excess of acid-acid anhydride mixture is typically equivalent to the quantity of solvent used in a normal reaction, although the actual quantity may be set as desired by the skilled person.

In the oxazolone ring forming reaction, amino groups or hydroxyl groups on peptide side chains may sometimes also undergo acylation with the carboxylic acid, at the same time as the oxazolone ring formation. If formic acid is used as the carboxylic acid, then these side chain functional groups undergo formylation. In the method of the first embodiment described above, these side chain functional groups are acetylated by the acetic anhydride, whereas in the method of the second embodiment, if formic acid is used, then the resulting side chain acyl groups can be removed more readily. Formyl groups introduced as a result of reaction with formic acid can be removed by a reagent such as hydroxylamine or hydrazine.

In this method that uses an active ester intermediate, the generated oxazolone compound is rapidly converted in-situ to the active ester through a ring-opening of the oxazolone ring, and as a result, side reactions such as hydrolysis of the oxazolone ring or sequential decomposition of the peptide chain can be effectively suppressed.

Following removal of the excess acid-acid anhydride mixture from the reaction solution under reduced pressure, the generated active ester can be used in the reaction described below.

The C-terminal of the protein or peptide, which has undergone active esterification in the manner described above, can be modified to any desired form by coupling with a compound containing a nucleophilic group. Examples of suitable compounds containing a nucleophilic group include the same compounds as those described above in relation to the first embodiment. If the compound containing a nucleophilic group is an amino group-containing compound represented by a general formula $XNH_2$, then one example of this coupling reaction is shown below in equation (IV).

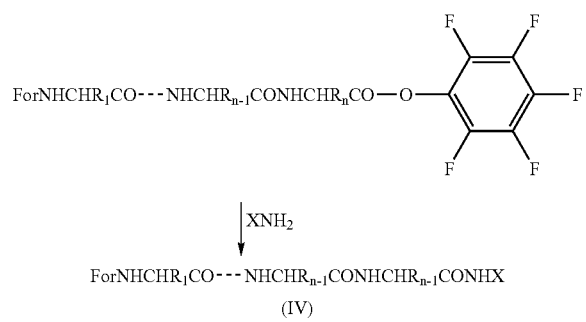

(IV)

This coupling reaction can be performed by stirring together the aforementioned active ester and the compound containing the nucleophilic group, in an appropriate solvent.

In this coupling reaction, there are no particular restrictions on the quantity of the compound containing the nucleophilic group. As described above, the active ester can be prepared for the subsequent coupling reaction by a simple treatment that involves placing the reaction solution under reduced pressure to remove the excess acid-acid anhydride mixture used in the ester synthesis. Following removal of this excess acid-acid anhydride mixture, the reaction container comprises a mixture of the active ester, and a by-product ester formed between the carboxylic acid and the active esterifying agent. In the coupling reaction, a side reaction can occur, in which this by-product ester partially acylates the compound containing the nucleophilic group. Depending on the active esterifying agent used, the compound containing the nucleophilic group may be needed in a quantity equal to, or even exceeding, the quantity of this by-product ester. However, in those cases where pentafluorophenol is used as the active esterifying agent, situations in which the quantity of by-product pentafluorophenyl ester exceeds the quantity of the compound containing a nucleophilic group actually provide comparatively better suppression of the partial acylation which is the side reaction of the coupling reaction, enabling the desired coupling reaction to proceed more efficiently.

The compound containing the nucleophilic group can be used in either solution form, or as a suspension. Examples of suitable solvents or liquids for suspension include the same organic solvents described in relation to the first embodiment, although in some cases, depending on the type of the active ester, water may also be used. For example, in those cases where p-nitrophenol is used as the active esterifying agent, the generated active ester is comparatively stable in aqueous solutions, meaning water can be used as the solvent.

The coupling reaction can be conducted under conditions including a temperature within a range from 0 to 200° C., and a reaction time from 1 minute to 48 hours. The reaction produces a reaction solution comprising a mixture of the targeted C-terminal-modified protein or peptide, generated by coupling between the compound containing the nucleophilic group and the protein or peptide, and a by-product produced by acylation of the compound containing the nucleophilic group by the aforementioned pentafluorophenol. Separation of, and differentiation between the two products can be performed easily using publicly known methods.

The method described above enables the selective modification of the C-terminal of a protein or peptide. For example, by using the modification method of the present invention to introduce an ionization-promoting material at the C-terminal of a protein or peptide, mass spectrometry techniques such as MALDI can be used to conduct high-sensitivity analysis. In a different example, by using the modification method of the present invention to label the C-terminal of a protein or peptide, MS/MS analysis can be used to achieve more reliable amino acid sequencing information. In addition, by performing sequential reactions of amino acid derivatives at the C-terminal, or by using a fragment condensation method, even peptide synthesis becomes possible.

EXAMPLES

As follows is a more detailed description of the present invention, based on examples in which the compound containing the nucleophilic group is either cysteic acid or arginine methyl ester, although the present invention is not restricted to the examples presented below.

Example 1

In this example, cysteic acid was introduced at the C-terminal of the peptide Z-Gly-Gly-Phe. In this peptide, the N-terminal is protected with a benzyloxycarbonyl group represented by the symbol Z.

To 41 mg (0.1 mmol) of the above peptide was added 0.5 ml of acetic anhydride, and the mixture was reacted for 15 minutes at 115° C. Following completion of the reaction, the acetic anhydride was removed under reduced pressure, and then two separate portions of toluene were added and subsequently removed under reduced pressure. To the resulting product was added a suspension comprising 17 mg of cysteic acid suspended in 0.5 ml of N-methylmorpholine, and the reaction was allowed to proceed overnight. Following completion of this reaction, the excess N-methylmorpholine was removed under reduced pressure. Subsequently, 1 ml of a 50% by weight aqueous solution of acetonitrile was added, and the resulting mixture was stirred for 3 hours. The resulting product was evaluated using MALDI-TOF MS. FIG. 1 shows the resulting spectrum. In FIG. 1, the horizontal axis represents Mass/Charge, and the vertical axis represents the relative intensity (% Int.) of the ion peak. As shown in FIG. 1, a peak was detected at 563.08 (m/z) using the negative ion detection mode, confirming that the target compound had been obtained.

Example 2

In this example, arginine methyl ester was introduced at the C-terminal of the peptide Z-Gly-Gly-Phe.

Figure 2:
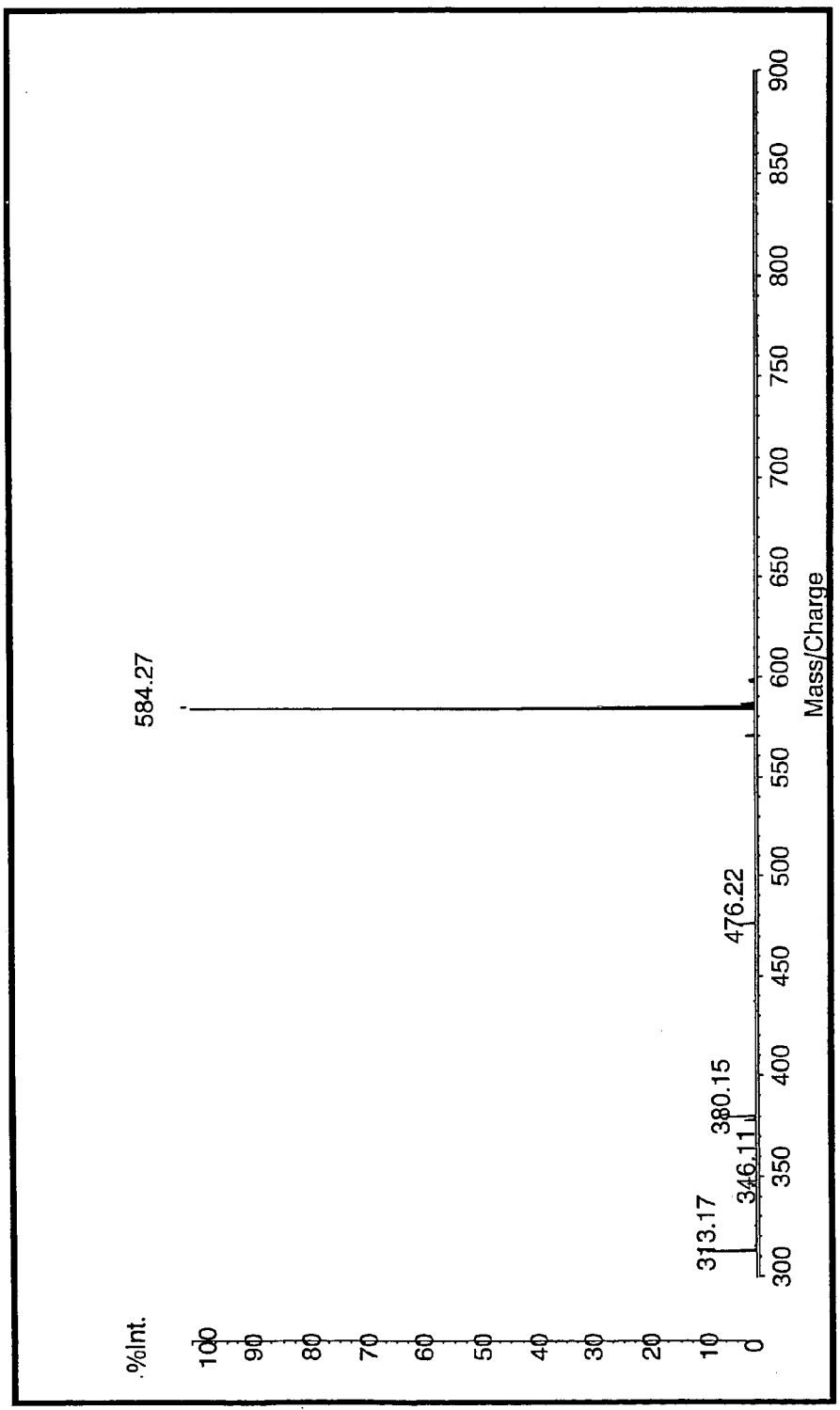
FIG. 2 is a MALDI-TOF MS spectrum obtained in an example of the present invention.

To 41 mg (100 μmol) of the above peptide was added 0.5 ml of acetic anhydride, and the mixture was reacted for 15 minutes at 115° C. Following completion of the reaction, the acetic anhydride was removed under reduced pressure, and then two separate portions of toluene were added and subsequently removed under reduced pressure. To the resulting product was added a suspension comprising 200 μmol of arginine methyl ester suspended in 0.5 ml of N-methylmorpholine, and the reaction was allowed to proceed overnight. Following completion of this reaction, the excess N-methylmorpholine was removed under reduced pressure. Subsequently, 1 ml of a 50% by weight aqueous solution of acetonitrile was added, and the resulting mixture was stirred for 3 hours. The resulting product was evaluated using MALDI-TOF MS. FIG. 2 shows the resulting spectrum. In FIG. 2, the horizontal axis represents Mass/Charge, and the vertical axis represents the relative intensity (% Int.) of the ion peak. As shown in FIG. 2, a peak was detected at 584.27 (m/z) using the positive ion detection mode, confirming that the target compound had been obtained.

Example 3

The C-terminal of leucine-enkephalin was subjected to active esterification, and this active ester was then coupled with arginine methyl ester.

2.8 mg (5 μmol) of leucine-enkephalin was dissolved in 0.5 ml of a 1:1 (volumetric ratio) mixture of formic acid and acetic anhydride, 18 mg (100 μmol) of pentafluorophenol was added, and once the crystals had dissolved, the solution was reacted for 20 minutes at 60° C. Following completion of the reaction, the solvent was removed under reduced pressure, and a process involving adding toluene to the residue and subsequently removing it under reduced pressure was repeated a number of times. To the resulting residue was added a solution produced by dissolving 26.1 mg (100 μmol) of arginine methyl ester dihydrochloride (H-Arg-OMe.2HCl) in 0.5 ml of water and then adding 50 μl of triethylamine to neutralize the hydrochloride, and the resulting mixture was stirred overnight at room temperature. The pH of the reaction liquid was from pH 9 to pH 10. The reaction product was analyzed directly using MALDI-TOF MS.

Figure 3:
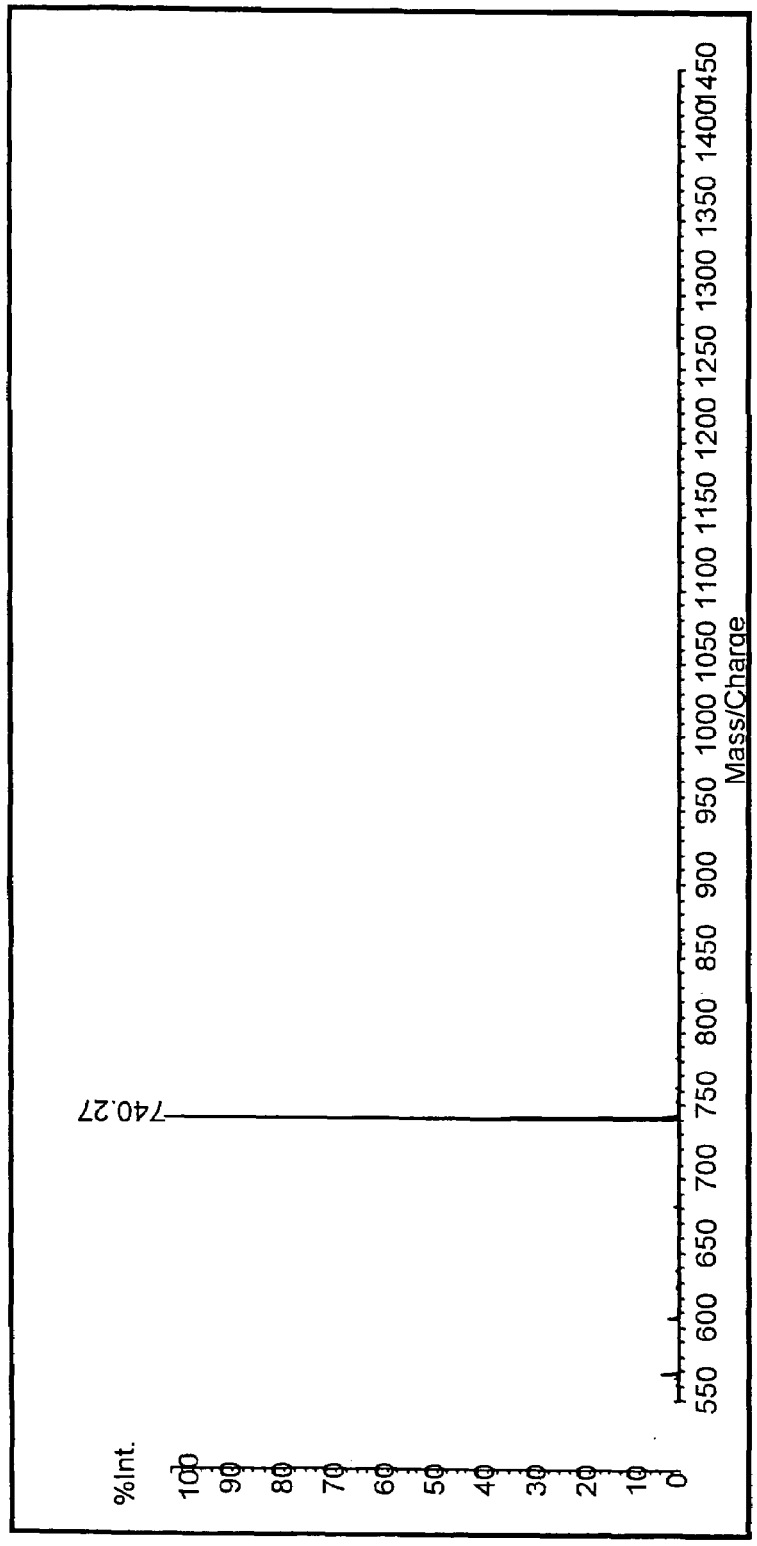
FIG. 3 is a MALDI-TOF MS spectrum obtained in an example of the present invention.

FIG. 3 shows the resulting spectrum. In FIG. 3, the horizontal axis represents Mass/Charge, and the vertical axis represents the relative intensity (% Int.) of the ion peak. As shown in FIG. 3, a peak was detected at 740.27 (m/z) using the positive ion mode, confirming that the target compound, in which the N-terminal had undergone formylation and the arginine methyl ester had undergone hydrolysis, had been obtained.

The examples described above represent three specific embodiments that fall within the scope of the present invention, but the present invention is not restricted to these examples, and a large variety of other embodiments are possible. Accordingly, in all respects the above examples represent mere illustrations, and these examples must not be considered as limiting the scope of the present invention. In addition, all modifications covered by the scope of the appended claims are considered part of the present invention.

What is claimed is:

1. A method for modifying the C-terminal of a protein or peptide, the method comprising the steps of:
    forming an intramolecular oxazolone ring at the C-terminal, of the protein or peptide that requires C-terminal modification; and
    performing a ring-opening of the oxazolone ring by reacting the oxazolone ring with a compound containing a nucleophilic group to produce a protein or peptide with a C-terminal modified with the compound containing the nucleophilic group.

2. The method for modifying the C-terminal of a protein or peptide according to claim 1, wherein the nucleophilic group is selected from the group consisting of an amino group, a hydroxyl group, and a thiol group.

3. The method for modifying the C-terminal of a protein or peptide according to claim 1, wherein the oxazolone ring is formed through the action of an acid anhydride.

4. The method for modifying the C-terminal of a protein or peptide according to claim 1, wherein the oxazolone ring is formed through the action of acetic anhydride.

5. The method for modifying the C-terminal of a protein or peptide according to claim 1, wherein the compound containing the nucleophilic group is reacted in the presence of a base.

6. The method for modifying the C-terminal of a protein or peptide according to claim 1, wherein by reacting the oxazolone ring with an active esterifying agent to effect a ring-opening, the oxazolone is converted to an active ester, which by subsequent reaction with a compound containing a nucleophilic group, produces a protein or peptide in which the C-terminal is modified with the compound containing the nucleophilic group.

7. The method for modifying the C-terminal of a protein or peptide according to claim 6, wherein the nucleophilic group is selected from the group consisting of an amino group, a hydroxyl group, and a thiol group.

8. The method for modifying the C-terminal of a protein or peptide according to claim 6, wherein the oxazolone ring is formed through the action of a mixture of an acid anhydride and a carboxylic acid.

9. The method for modifying the C-terminal of a protein or peptide according to claim 8, wherein the acid anhydride is acetic anhydride.

10. The method for modifying the C-terminal of a protein or peptide according to claim 8, wherein the carboxylic acid is formic acid.

11. The method for modifying the C-terminal of a protein or peptide according to claim 6, wherein the active esterifying agent is selected from the group consisting of pentafluorophenol, 4-sulfo-2,3,5,6-tetrafluorophenol, p-nitrophenol, N-hydroxysuccinimide, and N-hydroxybenzotriazole.

* * * * *